(12) United States Patent
Barth et al.

(10) Patent No.: US 6,843,281 B1
(45) Date of Patent: Jan. 18, 2005

(54) METHODS AND APPARATUS FOR INTRODUCING LIQUIDS INTO MICROFLUIDIC CHAMBERS

(75) Inventors: Phillip W. Barth, Portola Valley, CA (US); George E. Yefchak, Santa Clara, CA (US)

(73) Assignee: Agilent Techinologies, Inc., Palo Alto, CA (US)

( * ) Notice: Subject to any disclaimer, the term of this patent is extended or adjusted under 35 U.S.C. 154(b) by 0 days.

(21) Appl. No.: 10/632,175

(22) Filed: Jul. 30, 2003

(51) Int. Cl.[7] .................................................. B65B 1/04
(52) U.S. Cl. .............................. 141/5; 141/11; 141/69; 141/192; 137/803
(58) Field of Search ........................... 141/1, 5, 11, 31, 141/69, 192; 137/803, 825

(56) References Cited

U.S. PATENT DOCUMENTS 6,360,775 B1    3/2002  Barth et al.
6,365,378 B1    4/2002  Hirota et al.

OTHER PUBLICATIONS

U.S. patent application Publication: U.S. 2002/0115101 A1; Aug. 22, 2002.
U.S. patent application Publication: U.S. 2002/0122748 A1; Sep. 5, 2002.

Primary Examiner—Steven O. Douglas

(57) ABSTRACT

The present invention is directed to methods and apparatus for removing a gaseous bubble confined in a microvolume of liquid in a chamber. A source of liquid, a barrier region and an exit region are provided in fluid communication with the chamber. The source of liquid has an energy potential as regards movement of the gaseous bubble that is higher than the energy potential of the barrier region, the barrier region has a higher energy potential than the chamber, and the chamber has a higher energy potential than the exit region. The energy potential is reduced within the chamber, the source of liquid, the barrier region, and the exit region by an amount such that the energy within the gaseous bubble is sufficient to displace the gaseous bubble from the chamber through the barrier region and out the exit region and to fill the chamber with the liquid from the source.

14 Claims, 12 Drawing Sheets

METHODS AND APPARATUS FOR INTRODUCING LIQUIDS INTO MICROFLUIDIC CHAMBERS

BACKGROUND OF THE INVENTION

The present invention relates to microfluidic systems, and more particularly, to methods and apparatus for introducing and distributing fluid in channels of a microfluidic system. More particularly, the invention relates to filling microfluidic systems with liquids in a manner such that no gaseous bubbles are present in the system after filling, because such bubbles, if present, degrade the performance of the system. The microfluidic systems include, for example, microdroplet dispensing devices, microdevices with artificial nanopores, and the like.

In the field of diagnostics and therapeutics, it is often useful to attach species to a surface. One important application is in solid phase chemical synthesis wherein initial derivatization of a substrate surface enables synthesis of polymers such as oligonucleotides and peptides on the substrate itself. Substrate bound oligomer arrays, particularly oligonucleotide arrays, may be used in screening studies for determination of binding affinity. Modification of surfaces for use in chemical synthesis has been described. See, for example, U.S. Pat. No. 5,624,711 (Sundberg), U.S. Pat. No. 5,266,222 (Willis) and U.S. Pat. No. 5,137,765 (Farnsworth).

The arrays may be microarrays created on the surface of a substrate by in situ synthesis of biopolymers such as polynucleotides, polypeptides, polysaccharides, etc., and combinations thereof, or by deposition of molecules such as oligonucleotides, cDNA and so forth. In general, arrays are synthesized on a surface of a substrate or substrate by one of any number of synthetic techniques that are known in the art. In one approach, for example, the substrate may be one on which a single array of chemical compounds is synthesized. Alternatively, multiple arrays of chemical compounds may be synthesized on the substrate, which is then diced, i.e., cut, into individual assay devices, which are substrates that each comprise a single array, or in some instances multiple arrays, on a surface of the substrate.

The in situ synthesis methods include those described in U.S. Pat. No. 5,449,754 for synthesizing peptide arrays, as well as WO 98/41531 and the references cited therein for synthesizing polynucleotides (specifically, DNA). Such in situ synthesis methods can be basically regarded as repeating at each spot the sequence of: (a) deprotecting any previously deposited monomer so that it can now link with a subsequently deposited protected monomer; and (b) depositing a droplet of another protected monomer for linking. Different monomers may be deposited at different regions on the substrate during any one iteration so that the different regions of the completed array will have different desired biopolymer sequences. One or more intermediate further steps may be required in each iteration, such as oxidation, capping and washing steps. The deposition methods basically involve depositing biopolymers at predetermined locations on a substrate, which are suitably activated such that the biopolymers can link thereto. Biopolymers of different sequence may be deposited at different regions of the substrate to yield the completed array. Washing or other additional steps may also be used. Reagents used in typical in situ synthesis are water sensitive, and thus the presence of moisture should be eliminated or at least minimized.

Similar technologies can be used for in situ synthesis of biopolymer arrays, such as DNA oligomer arrays, on a solid substrate. In this case, each oligomer is formed nucleotide by nucleotide directly in the desired location on the substrate surface. This process demands repeatable drop size and accurate placement on the substrate.

As indicated above, one of the steps in the synthesis process usually involves depositing small volumes or microdroplets of liquid containing reagents for the synthesis, for example, monomeric subunits or whole polynucleotides, onto to surface of a support or substrate. In one approach, pulse-jet techniques are employed in depositing small volumes of liquid for synthesis of chemical compounds on the surface of substrates. For example, arrays may be fabricated by depositing droplets from a pulse-jet in accordance with known techniques. The pulse-jet includes piezo or thermal jets. Given the above requirements of biopolymer array fabrication, deposition using pulse-jet techniques is particularly favorable. In particular, pulse-jet deposition has advantages that include producing very small spot sizes. This allows high-density arrays to be fabricated. Furthermore, the spot size is uniform and reproducible. Since it is a non-contact technique, pulse-jet deposition does not result in scratching or damaging the surface of the support on which the arrays are synthesized. Pulse-jet techniques have very high deposition rate, which facilitates rapid manufacture of arrays.

However, a pulse jet deposition system used for fabricating a biopolymer array, should meet a number of requirements. The system should provide for reliable dispensing of the reagents and avoid deposition errors that can ruin the array fabrication. One requirement is that the presence of gaseous bubbles in the system must be minimized, eliminated, or prevented because gaseous bubbles present a problem of hydraulic compliance, which degrades system performance. Specifically, the pulse jet head must be capable of being loaded, or primed, with very small volumes of expensive DNA solution in a manner that minimizes, eliminates, or prevents gaseous bubbles without wasting that DNA solution in the priming process. Further, if gaseous bubbles occur in the pulse jet deposition system after the priming process, it must be possible to minimize or eliminate such bubbles without wasting that DNA solution in the process of minimization or elimination.

Considerable work is now underway to develop microfluidic systems, particularly for performing chemical, clinical, and environmental analysis of chemical and biological specimens. The term microfluidic system refers to a system or device having a network of chambers connected by channels, in which the channels have microscale features, that is, features too small to examine with the unaided eye, e.g., having at least one cross-sectional dimension in the range from about 0.1 $\mu$m to about 1 mm. Such microfluidic systems are often fabricated using photolithography, wet chemical etching, and other techniques similar to those employed in the semiconductor industry. The resulting devices can be used to perform a variety of sophisticated chemical and biological analytical techniques.

Microfluidic systems have a number of advantages over conventional chemical or physical laboratory techniques. For example, such microfluidic systems are particularly well adapted for analyzing small sample sizes, typically making use of samples on the order of nanoliters and even picoliters. The substrates may be produced at relatively low cost, and the channels can be arranged to perform numerous specific analytical operations, including mixing, dispensing, valving, reactions, detections, electrophoresis, and the like. The analytical capabilities of such microfluidic systems are generally enhanced by increasing the number and complexity of network channels, reaction chambers, and the like.

Efficient filling of a microfluidic system with liquid can be problematic because gas bubbles such as air bubbles can be trapped in the liquid flow path during introduction of the liquid into the microfluidic system. Such bubbles are difficult to remove from such systems. A number of approaches have been postulated for reducing or eliminating bubble formation during filling of microfluidic systems. For example, in one approach a piezoelectric system for dispensing DNA reagents is filled using degassed or deaerated liquids. The process begins with introducing a buffer solution, which is then replaced with an expensive reagent liquid containing a dissolved compound such as, for example, a DNA reagent. The object of this two-step procedure is to avoid introducing air bubbles into the flow path. However, the requirement of flushing the buffer solution with the expensive reagent liquid results in some waste of the expensive reagent liquid as well as waste of user time. See, for example, U.S. Patent Application Publication No. US 2002/0122748.

Recently, work has been conducted on microfluidic systems incorporating artificially fabricated nanopores. A nanopore is a hole through a membrane wherein the hole has a diameter less that approximately 100 nanometers (nm). Naturally occurring nanopore molecules can be found in the membranes of living cells. For example, the naturally-occurring alpha-hemolysin nanopore is a protein complex with a minimum internal diameter of 1.5 nm, which has been used in a simple microfluidic system to detect the passage of single-stranded oligonucleotide molecules. Artificially fabricated nanopores with diameters on the order of 2 to 100 nm have been fabricated by drilling holes in membranes of silicon nitride or silicon dioxide using a focused ion beam (FIB), followed by narrowing of the drilled hole using sculpting with a low-energy argon beam.

The process for establishing a liquid ionic conducting path through an artificially fabricated nanopore often presents difficulties. Such a pore may comprise a hole about 2 nm to about 70 nm in diameter in a membrane such as, e.g., silicon nitride or silicon dioxide, typically about 60 nm thick and about 50 $\mu$m in length and width. When such a pore is placed in a microfluidic system and the system is filled with an ionic buffer solution of potassium chloride (KCl), it is almost invariably found that an air bubble blocks electrical ionic conduction through the pore.

One approach to establishing conduction through an artificial nanopore is to first introduce a buffer solution of KCl in water to the structure holding the artificial nanopore, then place the system in a vacuum chamber and reduce the air pressure below atmospheric pressure. In this way, it is hoped that any trapped air bubbles in the system expand greatly and then leave the system when air pressure is increased again to atmospheric pressure. Unfortunately, this approach sometimes fails because, when the air pressure is increased, the trapped air bubble may return to its original position, leaving the nanopore blocked.

It is therefore desirable to provide improved structures, systems, and methods that overcome or substantially mitigate the problems set forth above. In particular, there exists a need in relation to the filling of microfluidic systems such as, for example, inkjet heads and artificial nanopore structures, for apparatus and methods that will reliably remove a gaseous bubble from a chamber without wasting liquids or time or both.

U.S. Pat. No. 6,360,775 (Barth, et al.) discloses a switching device for controlling fluid motion. The device includes a capillary filled with a first fluid into which a wall-confined bubble of a second fluid is introduced to achieve a first switching event. Capillary geometry and wetting properties provide a pressure-related asymmetric energy potential distribution for controlling the flow of the bubble, and the device is called an asymmetric bubble chamber, or ABC. The bubble is initially trapped in an energy potential well, and upon increase of its volume moves from the well into a region of low energy potential to achieve a second switching event. The first switching event may be blocking of a fluid channel or reflection of an optical beam in an optical crosspoint switch, while the second switching event may be unblocking of a fluid channel or restoration of transmission of an optical beam. The increase in bubble volume between the first and second switching events can act as the stroke of a fluidic piston to pump a volume of the first fluid within the capillary. The device can be employed to thermally degas a liquid. The use of large-magnitude geometry-related energy potentials permits rapid cyclical operation of the device in a manner resistant to mechanical shock.

SUMMARY OF THE INVENTION

In the present invention a trapped gaseous bubble is removed from a microfluidic system by means of reducing selected energy potentials of the system, where such energy potentials regard the energetics of movement of the bubble, to levels below the energy of the trapped bubble so that the bubble has enough energy to exit the system. The removal of the bubble achieves the purpose of complete liquid filling of the microfluidic system.

For purposes of description, the gaseous bubble is a bubble comprising a vapor of the liquid in which the bubble occurs, a gas or gas mixture other than the vapor of the liquid, or a combination of a vapor of the liquid and another gas or gas mixture. The bubble is considered to be trapped in a chamber region or "chamber." The chamber is in fluid communication with regions that function as a source of replacement fluid or "source", as an energy barrier region or "barrier," and as an exit region or "exit". The source, chamber, barrier, and exit regions each have distinct energy potential properties with respect to one another arising from differences in geometry, differences in construction materials, differences in surface layers, differences in applied voltages, which produce electrowetting effects, or a combination of one or more of the above.

In one embodiment of the present invention, the energy potentials each vary directly with the magnitude of ambient gas pressure surrounding the microfluidic system. In this embodiment, ambient pressure is reduced to a level below atmospheric pressure by means of placing the microfluidic system in a vacuum chamber and pumping out some of the ambient gas from the vacuum chamber. The number of moles of gas within the gas bubble may be substantially constant as is explained more fully below. As ambient pressure is reduced, the bubble expands, eventually displacing the bubble from the chamber, past the barrier, to the exit. Simultaneously with the movement of the bubble, liquid flows from the source into the chamber to leave the entire microfluidic system filled with degassed (deaerated) liquid. Then, the vacuum chamber is refilled with gas to return the ambient pressure to atmospheric pressure. The bubble may be exhausted from the exit to the vacuum chamber or vacuum manifold. Subsequently, one or more of the barrier and exit regions may be plugged to prevent liquid from leaving the device in an undesired manner. Accordingly, in the present invention the energy potentials of the source, the chamber, the barrier and the exit are decreased with respect to the energy of the bubble, the energy of the bubble being nearly constant, so that the bubble is removed.

The present invention differs from the method of Barth, et al., supra. In the present methods a microfluidic chamber is filled with a liquid by equalizing bubble pressure in the chamber with an applied pressure. The disclosure of Barth, et al., did not contemplate this method. In Barth, et al., the energy within a bubble is increased with respect to the energy potential of a source, a gate, a barrier and a drain to a level greater than the energy potential of the barrier region so that the bubble moves to achieve the desired switching. In the present invention the energy potentials of a liquid source, a chamber microvolume, a barrier region and an exit region of a chamber are decreased with respect to the energy of the bubble where the energy of the bubble is nearly constant, thus resulting in movement of the bubble out of the chamber.

One embodiment of the present invention is a method for removing a gaseous bubble confined in a microvolume of liquid in a chamber. A source of liquid, a barrier region and an exit region are provided in fluid communication with the chamber. The source of liquid has an energy potential as regards movement of the gaseous bubble that is higher than the energy potential of the barrier region, the barrier region has a higher energy potential than the chamber, and the chamber has a higher energy potential than the exit region. The energy potentials of the chamber, the source of liquid, the barrier region, and the exit region are reduced by an amount such that the energy within the gaseous bubble is sufficient to displace the gaseous bubble from the chamber through the barrier region and out the exit region and to fill the chamber with the liquid from the source.

Another embodiment of the present invention is a method of introducing a liquid into a chamber by means of a procedure that avoids the presence of a gaseous bubble at the end of the procedure, whether or not any gaseous bubble occurs in the chamber during the procedure. In this embodiment any possible gaseous bubble can be considered a "virtual bubble," that is; a bubble which may or may not actually occur but, if it occurs, is removed. The liquid is introduced into the chamber from a source of liquid. The source of liquid, a barrier region and an exit region are in fluid communication with the chamber. The source of liquid has an energy potential as regards movement of the gaseous bubble that is higher than the energy potential of the barrier region, the barrier region has a higher energy potential than the chamber, and the chamber has a higher energy potential than the exit region. The energy potential is reduced within the chamber, the source of liquid, the barrier region, and the exit region by an amount such that the energy within the gaseous bubble is sufficient to displace the gaseous bubble from the chamber through the barrier region and out the exit region and to fill the chamber with the liquid from the source.

Another embodiment of the present invention is an apparatus comprising a chamber, a source of liquid in fluid communication with the chamber, a barrier region in fluid communication with the chamber, an exit region in fluid communication with the barrier region, and an aperture in a wall of the chamber.

BRIEF DESCRIPTION OF THE DRAWINGS

The following figures are included to better illustrate the embodiments of the apparatus and technique of the present invention. The figures are not to scale and some features may be exaggerated for the purpose of illustrating certain aspects or embodiments of the present invention.

DETAILED DESCRIPTION OF SPECIFIC EMBODIMENTS

Figure 1A:
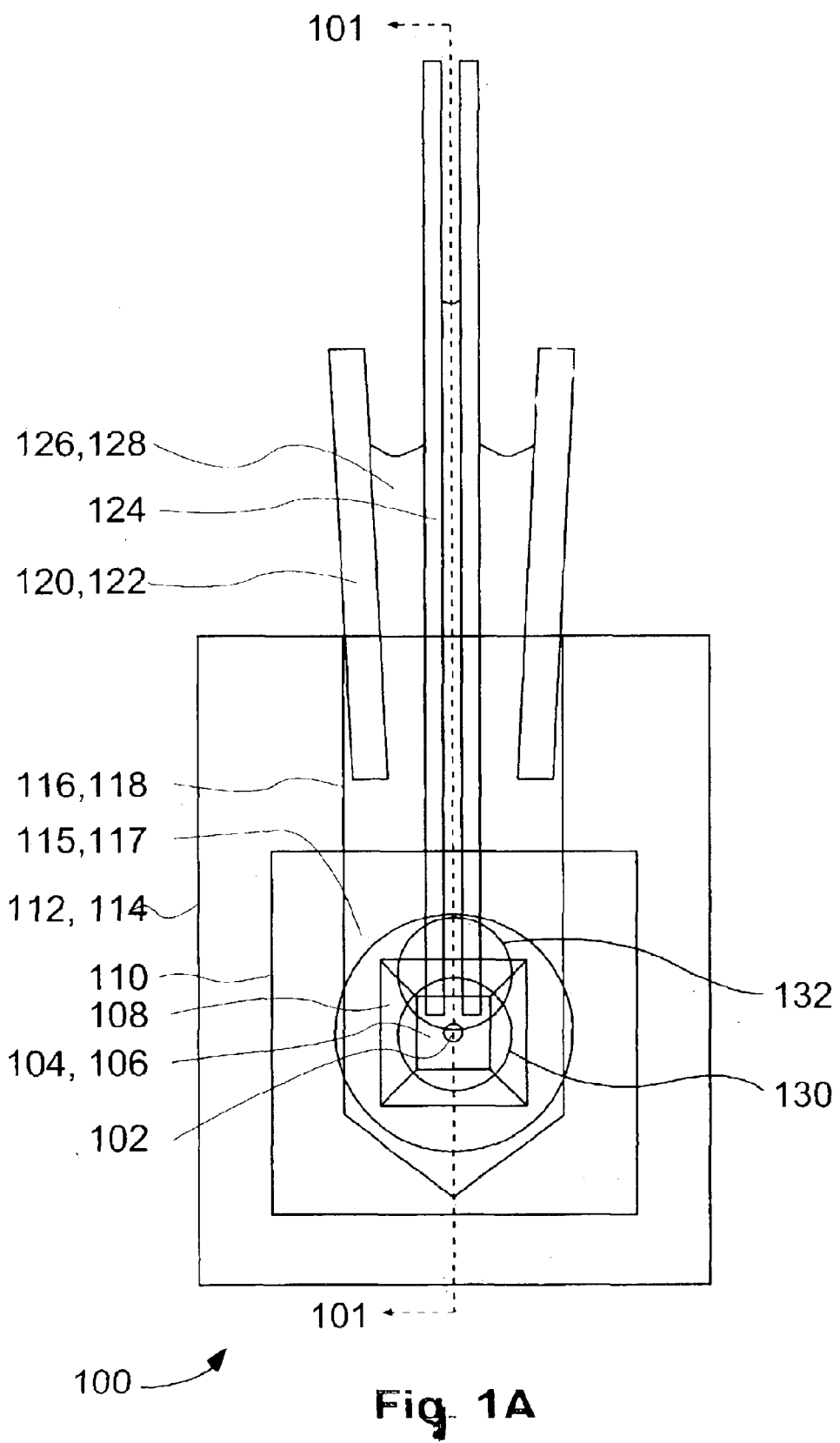
FIG. 1A is a wireframe view of one embodiment of the present invention.

As mentioned above, the present invention is directed to filling of a chamber with liquid while removing or avoiding gaseous bubbles that might otherwise result from such filling. The chamber is usually part of a microfluidic system. The term "microfluidic system" as used herein refers to a system or device having fluidic conduit features that are difficult or impossible to see with the naked eye, that is, having features on a scale of millimeters to tenths of micrometers. The size of the chambers is dependent on the particular application in which the chamber is used. Such chambers are found in microdevices such as droplet dispensing devices, devices with artificial nanopores, micro total analysis systems, and so forth. The present invention has application to any chamber that is to be filled with a liquid where the operation of the device after filling may be deleteriously affected by the presence of a gaseous bubble. The chambers may have internal volumes of about 1 picoliter to about 50 microliters and may in certain circumstances be larger or smaller than the aforementioned volumes. The terms "filling" and "fill" are used herein to mean introducing liquid into the chamber to occupy at least about 98% of the volume, at least about 99% of the volume, usually about 100% of the volume, of the chamber.

The materials from which the chambers and related components may be fabricated are dependent on the particular environment or use of the chamber, the nature of the liquid within the chamber, the desired differences in energy potentials in accordance with the present invention, the advantages and limitations of particular fabrication techniques, and so forth. Materials include polymers, plastics, resins, polysaccharides, silica or silica-based materials, carbon, metals including metal alloys, metal oxides, inorganic glasses, and so forth. Particular plastics finding use include, for example, polyethylene, polypropylene, such as high density polypropylene, polytetrafluoroethylene (PTFE), e.g., TEFLON®, polymethylmethacrylate, polycarbonate, polyethylene terephthalate, polystyrene or styrene copolymers, polyurethanes, polyesters, polycarbonates, polyureas, polyamides, polyethyleneamines, polyarylene sulfides, polysiloxanes, polydimethylsiloxanes, polyimides, polyacetates, poly etheretherketone (PEEK), and the like. Metals include, for example, stainless steel, hastalloy, platinum, gold, silver, titanium, and so forth.

The interior of the chamber, the barrier region, the exit region, the source of liquid, and the like may be coated with a material that functions to change the energy properties of the surfaces of any of the above. The coating may be any of the aforementioned materials placed on the surface of the material from which the chamber or one or more of its components are fabricated.

The present devices may be fabricated as unitary devices or they may be constructed from several parts assembled into the device. Apertures may be made in the chamber housing by laser cutting, etching, piercing, drilling, punching, direct molding or casting from a master with pins, and so forth.

Droplet dispensing devices usually comprise one or more chambers, which are filled with liquid to be dispensed. Typically, a chamber has at least one aperture or orifice, usually, one aperture or orifice, which is a micropore and through which droplets are dispensed. A micropore is a pore (or aperture or orifice) that is small usually on the order of micrometers (or micron scale) or less. The size of the micropore as it relates to the present invention is usually about 2 $\mu$m to about 50 $\mu$m, more usually, about 4 $\mu$m to about 40 $\mu$m. The chamber is in fluid communication with a source of liquid, which may be contained in one or more reservoirs that are connected to the chamber by suitable conduits and valves. The droplet dispensing devices also include a means for causing the droplet to be dispensed, for example a piezoelectric driver element or a thermal driver element.

A number of approaches have been developed for accurately dispensing small drops of liquid and depositing them onto solid substrates. For example, inkjet printers utilize piezoelectric dispensers to dispense liquid drops at rates of up to at least 2,000 drops per second. In one such system (known as a continuous device) a fluid under pressure issues from an orifice in a dispenser while a piezoelectric crystal attached to the dispenser induces pressure oscillations in the fluid causing the fluid stream to break into drops after issuing from the dispenser. The drops form in the presence of an electrostatic field and thus acquire an electric charge. As the drops continue toward the substrate, they pass through another electrostatic field, which interacts with their acquired charge to deflect them to a desired location.

In another inkjet system fluid from a reservoir is fed into a dispenser and a piezoelectric crystal directly or indirectly coupled to the fluid responds to a voltage pulse to induce a volume change in the dispenser, thus causing a drop of fluid to issue from an orifice toward a substrate. In this type of dispenser (known as a drop-on-demand device) a drop is formed only in response to a predetermined voltage pulse.

In addition to using piezoelectric effects, inkjets may also use heat to form and propel drops of fluid. Thermal inkjets heat a fluid so rapidly that the fluid vaporizes. Rapid volumetric changes provide the impetus for propelling drops of fluid or ink from the dispenser. Bubble jet printers also function on similar principals.

The aforementioned jetting systems have been adapted to dispense liquid reagents to a surface for conducting chemical reactions such as in the analysis of analytes, synthesis of chemical compounds, and the like. For example, in the manufacture of nucleic acid arrays, inkjets can be used to deposit nucleic acids on the substrate surface. See, for example, U.S. Pat. No. 5,658,802. U.S. Pat. No. 5,338,688 describes the use of a bubble-jet for similar applications. The present invention has application in all of the above systems.

As mentioned above, microfluidic systems include microdevices with nanopores, usually, artificial nanopores. The term microfluidic system refers to a system or device having a network of chambers connected by channels, in which the channels have mesoscale dimensions, e.g., having at least one cross-sectional dimension in the range from about 0.1 $\mu$m to about 500 $\mu$m. Typically, a chamber has at least one aperture or orifice, which is a nanopore, i.e., a small pore (or aperture or orifice) on the order of nanometers (i.e., nanometer scale). Materials in a liquid contained within the chamber are moved through the nanopore. The size of the nanopore is usually about 0.5 nm to about 100 nm, more usually, about 1.5 nm to about 30 nm. In one example, a microfluidic fluid delivery system may include a microfluidic device having a fluid input. A fluid reservoir is fluid communication with the fluid input. The aforementioned devices may also include means for introducing liquids into the devices as well as means for moving materials in the liquids within the devices. The resulting devices can be used to perform a variety of sophisticated chemical and biological analytical techniques.

In one approach, microfluidic systems are employed to separate materials in a microchannel and move the materials through microchannels. Moving the materials through microchannels is possible by use of a fluid pressure difference and by use of various electro-kinetic processes including electrophoresis, electroosmotic flow, and electrokinetic pumping. Microfluidic devices have been designed that are useful in performing high throughput assays useful for biological and chemical screening experiments. Glass polymer, semiconductor, ceramic, and metallic microfluidic devices comprising microfluidic channels and microfluidic wells are now available. Continuous flow microfluidic systems are useful, for example, in screening large numbers of different compounds for their effects on a variety of chemical and biochemical systems. The devices include a series of channels fabricated on or within the devices. The devices also can include reservoirs, fluidly connected to the channels, which can be used to introduce a number of test compounds into the sample channels and thus perform the assays. Interfacing mechanisms, such as electropipettors, can be incorporated into these high-throughput systems for transporting samples into wells or microfluidic channels.

Microfluidic systems for fast, accurate and low cost electrophoretic analysis of materials in the fields of chemistry, biochemistry, biotechnology, molecular biology and numerous other fields are described in U.S. Pat. No. 5,699,157. Techniques for transporting materials through microfluidic channels using electrokinetic forces are described in U.S. Pat. No. 5,799,868. Movement of material through microfluidic channels is further described in U.S. Pat. No. 5,800,690.

Regardless of the particular environment in which the chamber is found, the benefits of the present invention are realized by providing, in fluid communication with the chamber, a source of fluid, a barrier region and an exit region. The barrier region has energy potential as regards movement of the gaseous bubble that is higher than the energy potential of the exit region and higher than the energy potential of the chamber. The source of liquid has a higher energy potential than the barrier region. The chamber has a higher energy potential than the exit region. Typically, a gaseous bubble is present in the chamber that is preventing the chamber from filling with a predetermined volume of liquid, usually, a microvolume of liquid that corresponds to the capacity volume of the chamber. The gaseous bubble may present an undesirable mechanical compliance to the ejection of liquid from the chamber by pulsejet means. Alternatively, the gaseous bubble may prevent an ionic electrical conduction path from being established through a nanopore in fluid communication with the chamber. On the other hand, the bubble may be interfering with the passage of a material such as, for example, particles such as charged particles, e.g., positive and negative ions, solid particles present as a slurry in the liquid, molecules dissolved in the liquid and the like, through an aperture that provides an exit from the chamber other than the aforementioned exit region, for example, through the firing orifice of an inkjet device. The bubble is usually confined in the microvolume of liquid. It is important to note that not all gaseous bubbles within one or more chambers of a microfluidic device conflict with the ability to move materials through an aperture. In the latter circumstance, it is not necessary to remove such a bubble from a chamber.

The source, chamber, barrier, and exit regions each have distinct energy potential properties with respect to one another arising from differences in geometry, differences in construction materials, differences surface layers, differences in applied voltages that produce electrowetting effects, or a combination of one or more of the above.

The barrier region is normally situated between the exit region and the microvolume of fluid in which the gaseous bubble resides such that the gaseous bubble enters the barrier region before the exit region in a spatial sense. To achieve a difference in energy potential as a result of a difference in material of composition of the barrier region and the exit region, the hydrophobicity or hydrophilicity of the materials or coatings on the interior surfaces of the materials may be considered.

The source of liquid may be positioned in any area of the chamber such that liquid is introduced into the chamber coincident with the removal of a gaseous bubble therefrom. In one embodiment the source of liquid is adjacent the barrier region and the exit region. In another embodiment, the source of liquid is through the barrier region and the exit region.

As mentioned above, the source of liquid has an energy potential as regards movement of the gaseous bubble that is higher than the energy potential of the barrier region, the barrier region has a higher energy potential than the chamber, and the chamber has a higher energy potential than the exit region.

A chamber may have one of many cross-sectional shapes such as a square, rectangular, trapezoidal, circular, oval, etc., cross section. Furthermore, the cross-section of the interior of a chamber may have several different cross-sectional shapes. For example, the cross-sectional shape of an area of the chamber adjacent a pore or opening or orifice may be different than that of the remainder of the chamber. A "candidate bubble" in a chamber is a bubble that must be removed because the bubble is blocking transport of materials through an opening in the chamber or is preventing the filling of the chamber with liquid for expulsion through an opening. Usually, at least a portion of the periphery of the bubble is in contact with the walls of the chamber. Where the bubble is preventing the transport of materials through an opening, a portion of the periphery of the bubble is in, contact with the interior walls of the chamber immediately adjacent the opening. Where the bubble is preventing filling of the chamber, the bubble may be at any location within the chamber.

Between a fluid bubble such as a gas bubble and its fluid surroundings such as a liquid, there exists an interfacial surface which can be characterized by a radius of curvature r and a surface tension a (T), where T is temperature and so a is a function of temperature T. Across this surface there exists a pressure difference given by $P=2\sigma(T)/r$ (see, for example, Physical Chemistry, Walter J. Moore, fourth edition, Prentice-Hall, Englewood Cliffs, N.J., page 478).

The bubble surface can be manipulated by varying one or more of the pressure difference, the surface tension, the surface radius of curvature, and the wetting properties of the capillary walls.

Good wetting and poor wetting can be quantified in terms of equilibrium contact angles of fluid against a surface. For example, a drop of water in air contacting a clean plate of silicon dioxide glass has a very low equilibrium contact angle taken within the water, and the glass surface is said to be well wetted. However, the contact angle taken within the air is large, and so the air is considered to "wet" poorly in comparison to water. On the other hand, a drop of mercury in air resting on a clean glass plate has a very high equilibrium contact angle taken within the mercury droplet. The glass surface is said to be poorly wetted by the mercury, and the air is considered to wet well in comparison to the mercury. For aqueous liquids good wetting is called hydrophilicity and is characterized by an equilibrium contact angle less than ninety degrees; the wetted material is described as hydrophilic. Similarly, poor wetting is called hydrophobicity and is characterized by an equilibrium contact angle greater than ninety degrees; the wetted material is described as hydrophobic. The terms hydrophilic and hydrophobic can be generalized to "fluiphilic" and "fluiphobic" to describe the equilibrium contact angle taken within any fluid where it meets a second immiscible fluid at a solid wall.

The energy potential of a region for a gaseous bubble in a liquid in a chamber can be influenced both by geometry and by temperature. For example, for a bubble of gas within a liquid that is fluiphilic to the capillary walls of a liquid source, narrow capillaries have a higher energy potential than wider capillaries, and cooler regions have a higher energy potential than warmer regions. The above are some of the factors that may be controlled to achieve the differences in energy potential between the source of liquid and the barrier region, the barrier region and the chamber and the chamber and the exit region.

In the next step in accordance with the method of the present invention, the energy potential is reduced within the chamber, the source of liquid, the barrier region, and the exit region by an amount sufficient that the energy within the gaseous bubble is sufficient to displace the gaseous bubble from the chamber through the barrier region and out the exit region and to fill the chamber with the liquid from the source.

The energy contained within a bubble due to pressure is just the internal pressure of the bubble with respect to its surroundings multiplied by the volume of the bubble. Thus, the pressure is one measure of the energy. Other factors such as gravity and temperature can contribute their own energy.

Accordingly, one approach to reducing the energy potential within the chamber, the source of liquid, the barrier region and the exit region is to reduce hydrostatic pressure in these regions. To this end, ambient pressure may be reduced by placing the microfluidic system in a vacuum housing and applying a vacuum in a continuous manner so as to reduce ambient pressure to a level below that of the internal pressure of the bubble. Once the gaseous bubble has been removed from the chamber through the exit region the pressure surrounding the microfluidic system is returned to its original level, usually, ambient level.

As mentioned above, in one embodiment of the present invention, the energy potentials each vary directly with the magnitude of ambient gas pressure surrounding the microfluidic system. In this embodiment, ambient pressure is reduced to a level below atmospheric pressure by means of placing the microfluidic system in a vacuum chamber and pumping out some of the ambient gas from the vacuum chamber. The number of moles of gas within the gas bubble may be substantially constant, which may be explained more fully as follows. As is well known, when the ambient pressure surrounding a liquid is reduced, any gas dissolved in that liquid tends to leave the liquid in accordance with Henry's Law as the partial pressure of the gas in the ambient is reduced below the partial pressure of the gas in the liquid. This process of gas leaving the liquid can result in the generation of gaseous bubbles, or in the enlargement of existing gaseous bubbles, either of which events increases the number of moles of gas in a bubble and increases the size of a gaseous bubble at constant ambient pressure. However, such an increase in the number of moles of gas in a bubble may be regarded as inadvertent and unavoidable as regards the action of the present invention wherein the size of a gaseous bubble increases due to a reduction in pressure while the number of moles of gas in the bubble is substantially constant. In any event the present invention works regardless of whether or not additional gas enters a bubble.

As is also well known, the boiling temperature of a liquid commonly decreases as the ambient pressure of gas surrounding the liquid decreases. Thus, a liquid at room temperature can begin to boil as the ambient pressure of the gas surrounding the liquid decreases. This process of boiling due to reduction in ambient pressure can result in the generation of gaseous bubbles, or in the enlargement of existing gaseous bubbles, either of which events increases the number of moles of vapor in a gaseous bubble and increases the size of a gaseous bubble at constant ambient pressure. However, such an increase in the number of moles of vapor in a bubble may be regarded as inadvertent and unavoidable as regards the action of the present invention wherein the size of a gaseous bubble increases due to a reduction in pressure while the number of moles of vapor in the bubble is substantially constant. It is well known that when a liquid boils due to a reduction in ambient pressure, the temperature of the liquid falls, and that such a liquid eventually stops boiling in the absence of a further input of thermal energy from its surroundings. In any event the present invention works regardless of whether or not additional vapor enters a bubble.

As ambient pressure is reduced in accordance with the present invention, the bubble expands, eventually displacing the bubble from the chamber, past the barrier, to the exit. Simultaneously with the movement of the bubble, liquid flows from the source into the chamber to leave the entire microfluidic system filled with degassed (deaerated) liquid. Then, the vacuum chamber is refilled with gas to return the ambient pressure to atmospheric pressure. The bubble may be exhausted from the exit to the vacuum chamber or vacuum manifold. Subsequently, one or more of the barrier and exit regions may be plugged to prevent liquid from leaving the device in an undesired manner. Accordingly, in the present invention the energy potentials of the source, the chamber, the barrier and the exit are decreased with respect to the energy of the bubble, the energy of the bubble being nearly constant, so that the bubble is removed.

Figure 1B:
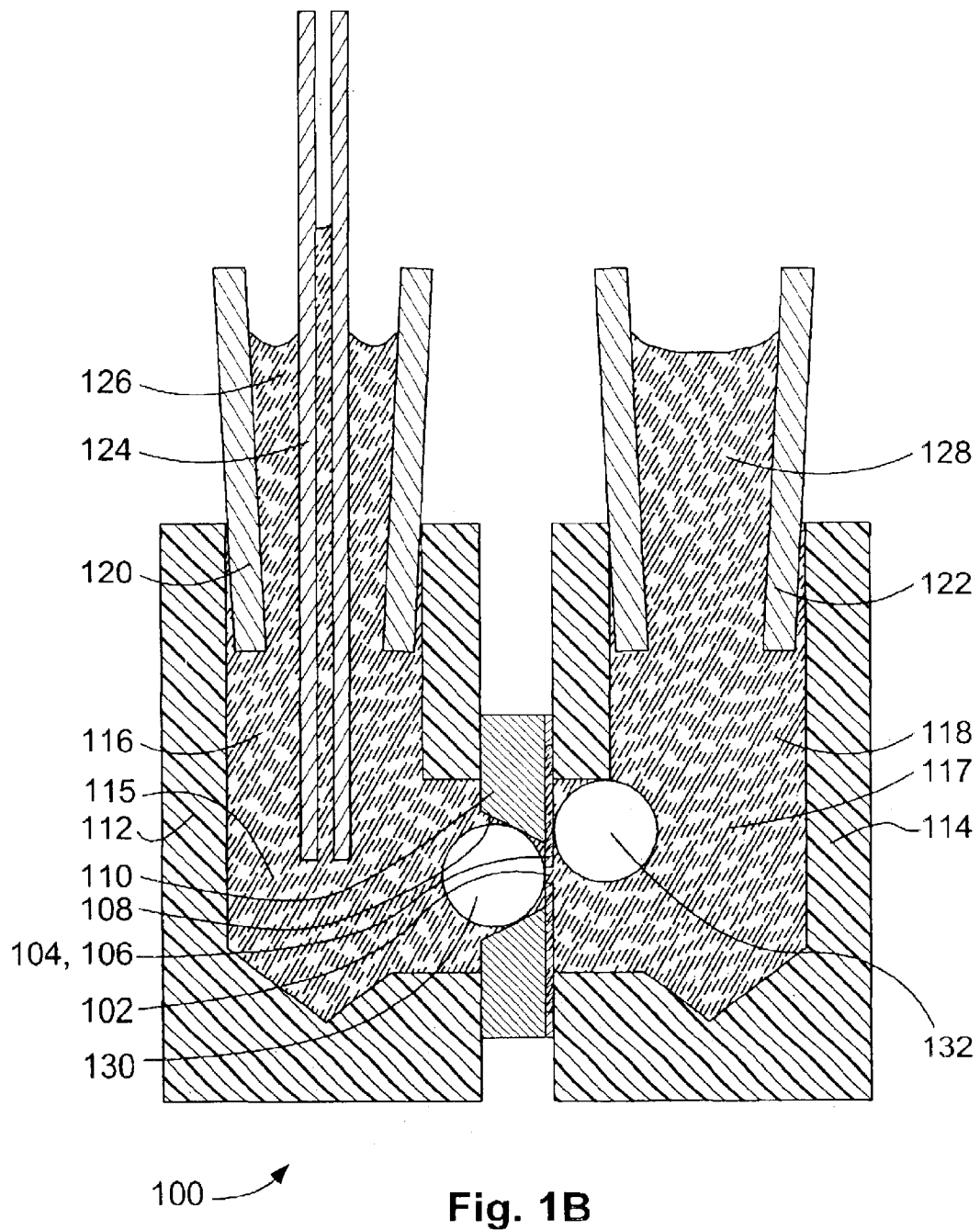
FIG. 1B is a cross-sectional view of the embodiment of FIG. 1A taken along section line 101 at one point in time.

FIGS. 1A–1H illustrate, by way of example and not limitation, an embodiment 100 of the invention as it is applied to priming an artificial nanopore. As mentioned above, FIG. 1A is a wireframe view of embodiment 100, and section line 101 denotes the cross section of embodiment 100 shown at sequential time steps in FIGS. 1B–1H. FIG. 1B corresponds in time to FIG. 1A, while FIGS. 1C–1H correspond to subsequent times.

Nanopore 102 extends through freestanding window 104, which forms part of layer 106. Layer 106 is surrounded by sloping sidewalls 108 situated in silicon chip 110. Silicon chip 110 is supported between housing members 112 and 114, which contain passages 116 and 118, respectively, to form two chambers 115 and 117. Tapered tubes 120 and 122 are secured into place in passages 116 and 118 to aid in liquid filling and degassing. Tube 124, which corresponds to a source of liquid, is used as part of the invention to aid in filling passage 116 with liquid volume 126. Passage 118 is filled with liquid volume 128. Bubble 130 is a gaseous bubble within liquid volume 126, and bubble 132 is a gaseous bubble within liquid volume 128. Gaseous bubble 130 blocks the free flow of particles through nanopore 102 and is held in place by adhesion forces to window 104 and sidewalls 108. For the nanopore to function as desired, bubble 130 must be removed. The structure and method of the present invention are utilized to remove bubble 130.

Gaseous bubble 132 is so situated that it does not block the free flow of particles through nanopore 102, and it is not necessary to remove bubble 132; thus it is not necessary to implement the structure and method of the present invention in conjunction with features 114, 118, 122, 128, and 132 on the right-hand side of FIG. 1B.

Figure 1C:
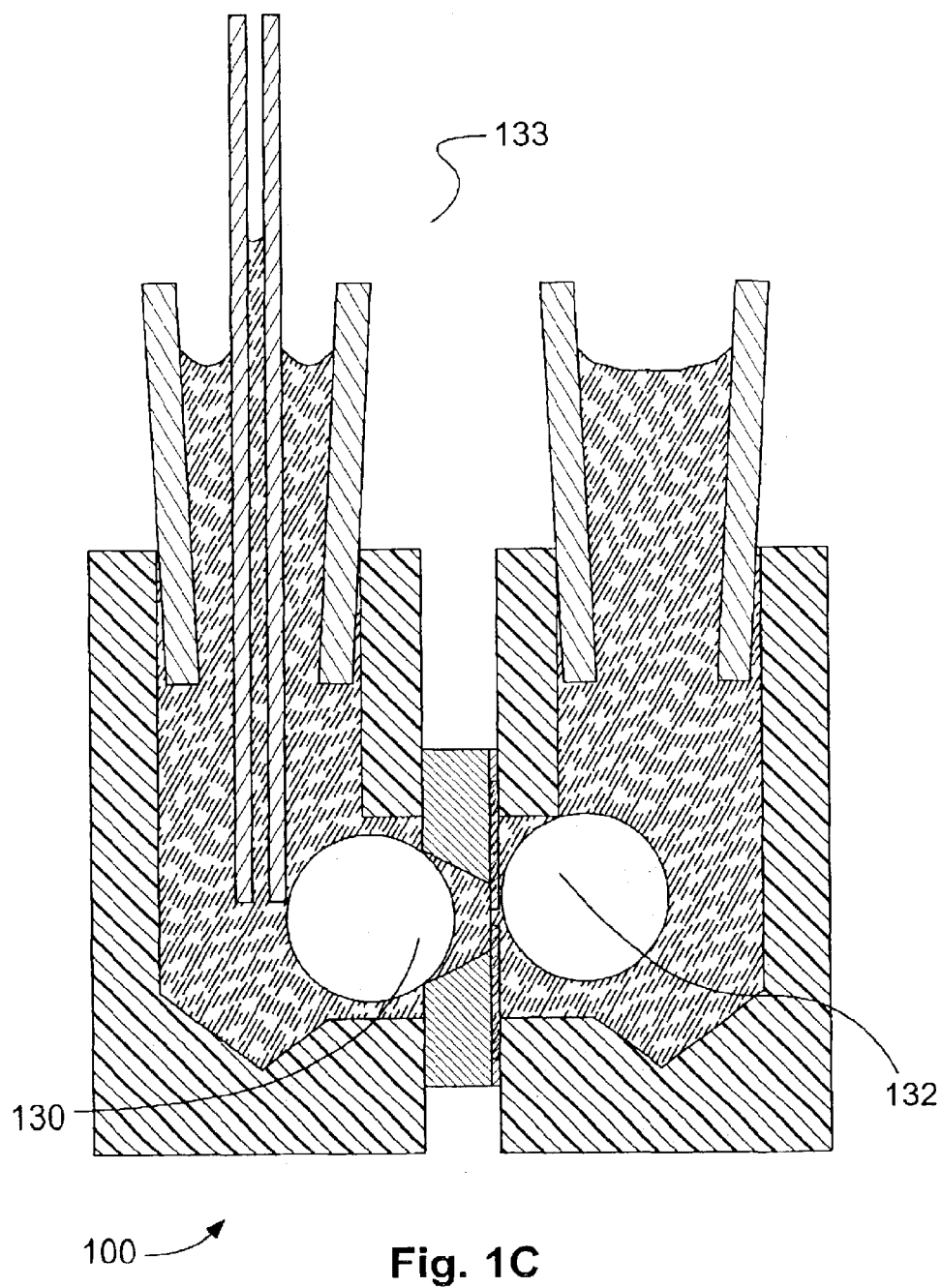
FIG. 1C is a cross-sectional view of the embodiment of FIG. 1A taken along section line 101 at another point in time.

FIG. 1C illustrates embodiment 100 at a time subsequent to the time of FIG. 1B. Embodiment 100 has been placed in a vacuum housing, not shown, and ambient atmosphere 133 has been reduced in pressure to a value below atmospheric pressure by pumping on the vacuum housing using a vacuum pump, not shown. As ambient atmosphere 133 is reduced in pressure, bubbles 130 and 132 expand in volume.

Figure 1D:
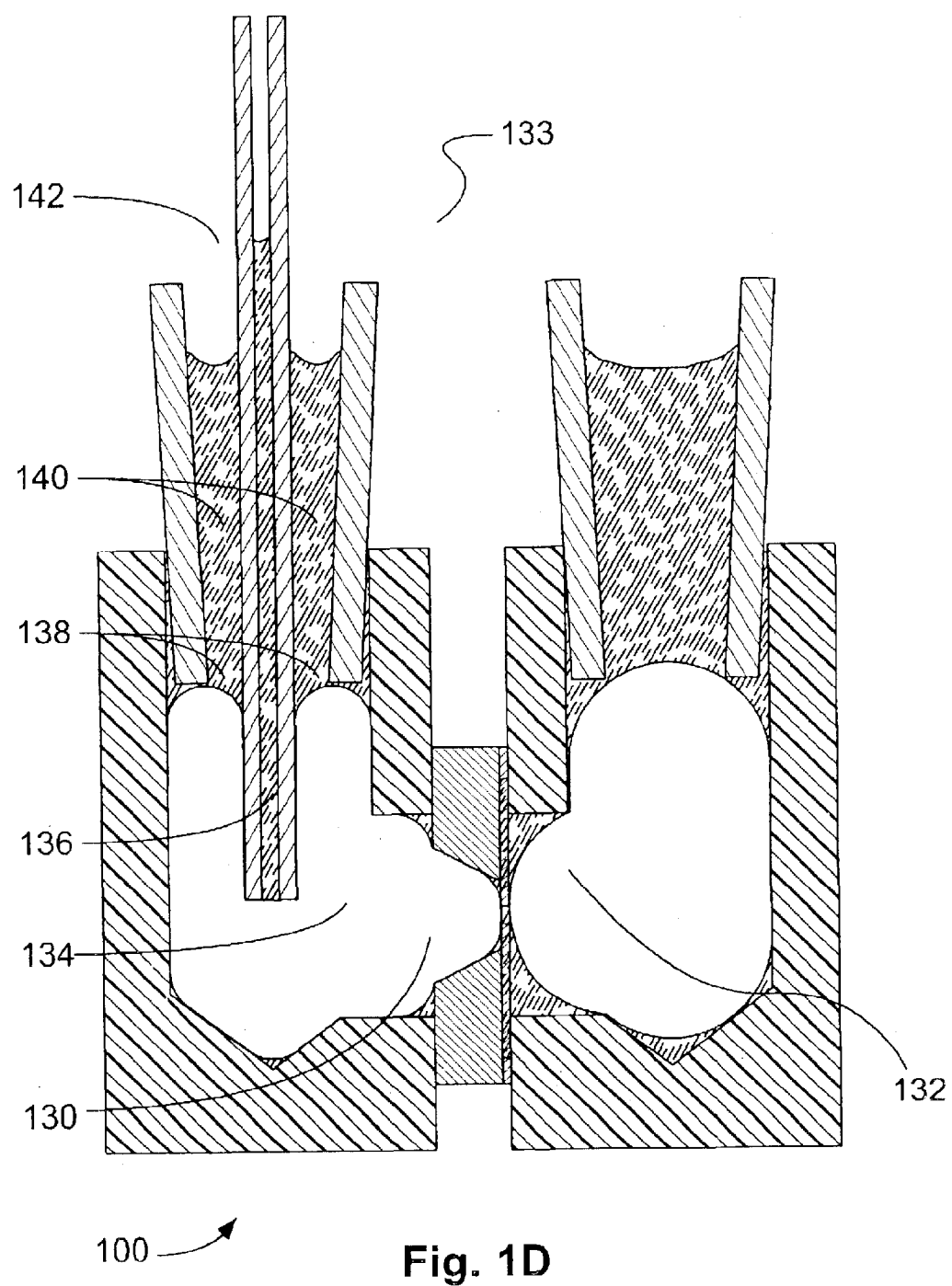
FIG. 1D is a cross-sectional view of the embodiment of FIG. 1A taken along section line 101 at another point in time.

FIG. 1D shows embodiment 100 at a time subsequent to the time of FIG. 1C. Ambient atmosphere 133 has been further reduced in pressure, and bubbles 130 and 132 have further expanded in volume. Bubble 130 fills a volume 134. Channel 136 comprises a source channel for liquid, narrow region 138 comprises a barrier region, and channel 140 and ambient gaseous volume 142 comprise an exit region.

Figure 1E:
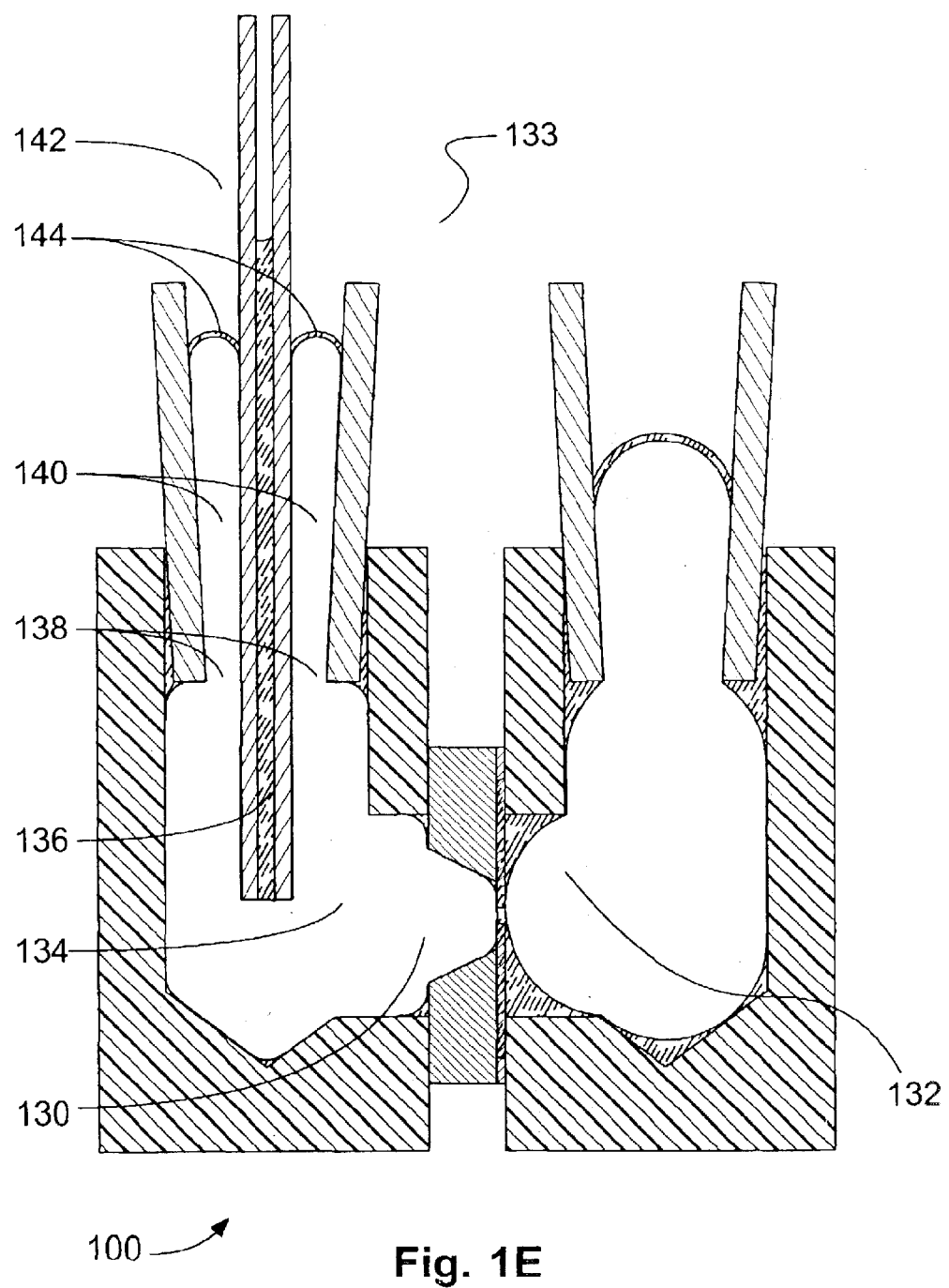
FIG. 1E is a cross-sectional view of the embodiment of FIG. 1A taken along section line 101 at another point in time.

FIG. 1E shows embodiment 100 at a time subsequent to the time of FIG. 1D. Ambient atmosphere 133 has been further reduced in pressure, and bubbles 130 and 132 have further expanded in volume. Bubble 130 has expanded past the narrow barrier region 138, and the radii of curvature of bubble boundary 144 are increasing as this boundary moves up in channel 140.

Figure 1F:
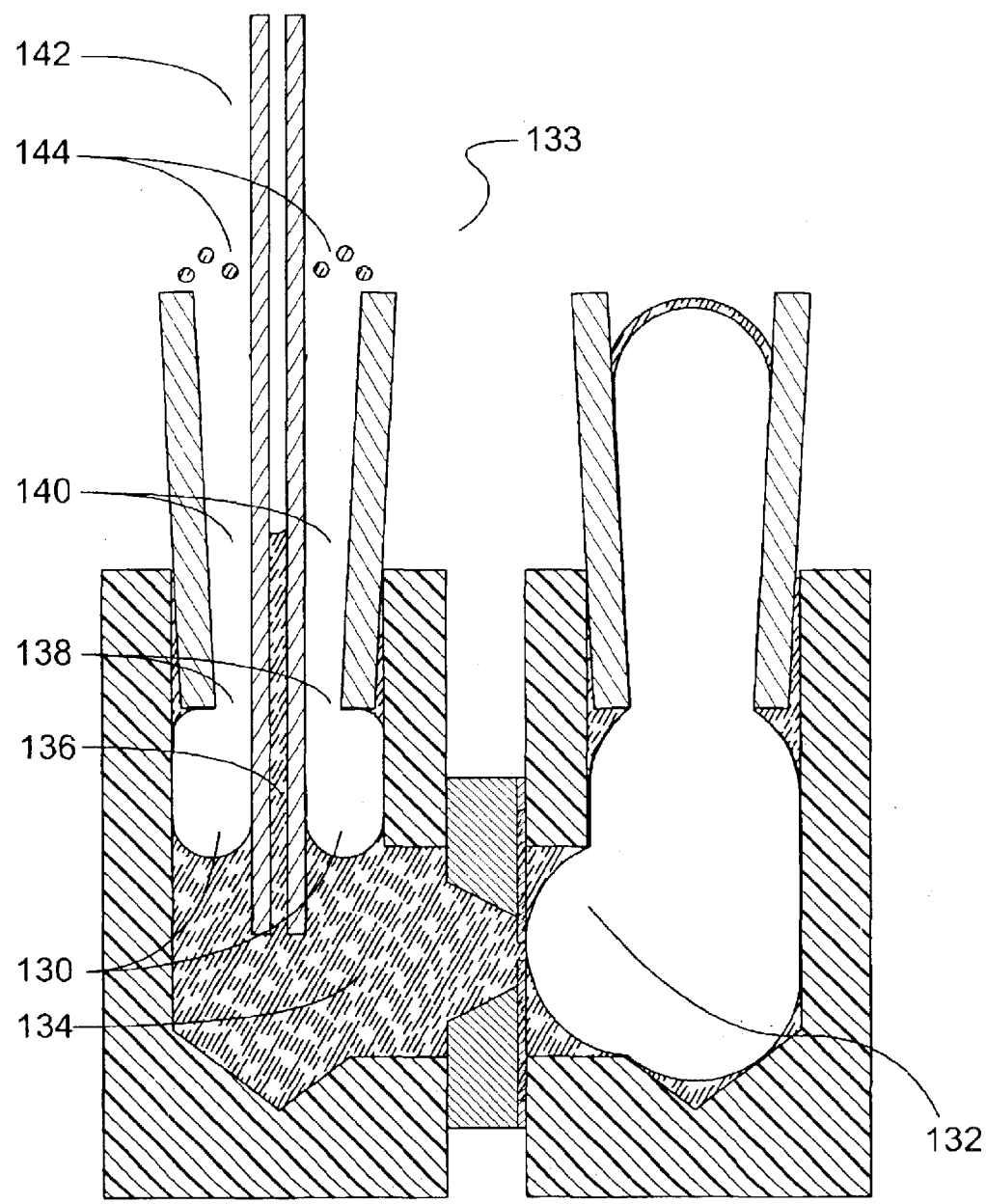
FIG. 1F is a cross-sectional view of the embodiment of FIG. 1A taken along section line 101 at another point in time.

FIG. 1F shows embodiment 100 at a time subsequent to the time of FIG. 1E. Ambient atmosphere 133 has been further reduced in pressure, and bubble 132 has expanded further in volume. But bubble 130 has burst at boundary 144, and the gaseous volume of bubble 130 exiting past barrier region 138 through the exit region comprising channel 140 and ambient gaseous volume 142 as the gate volume 134 is refilled with liquid supplied by source channel 136.

Figure 1G:
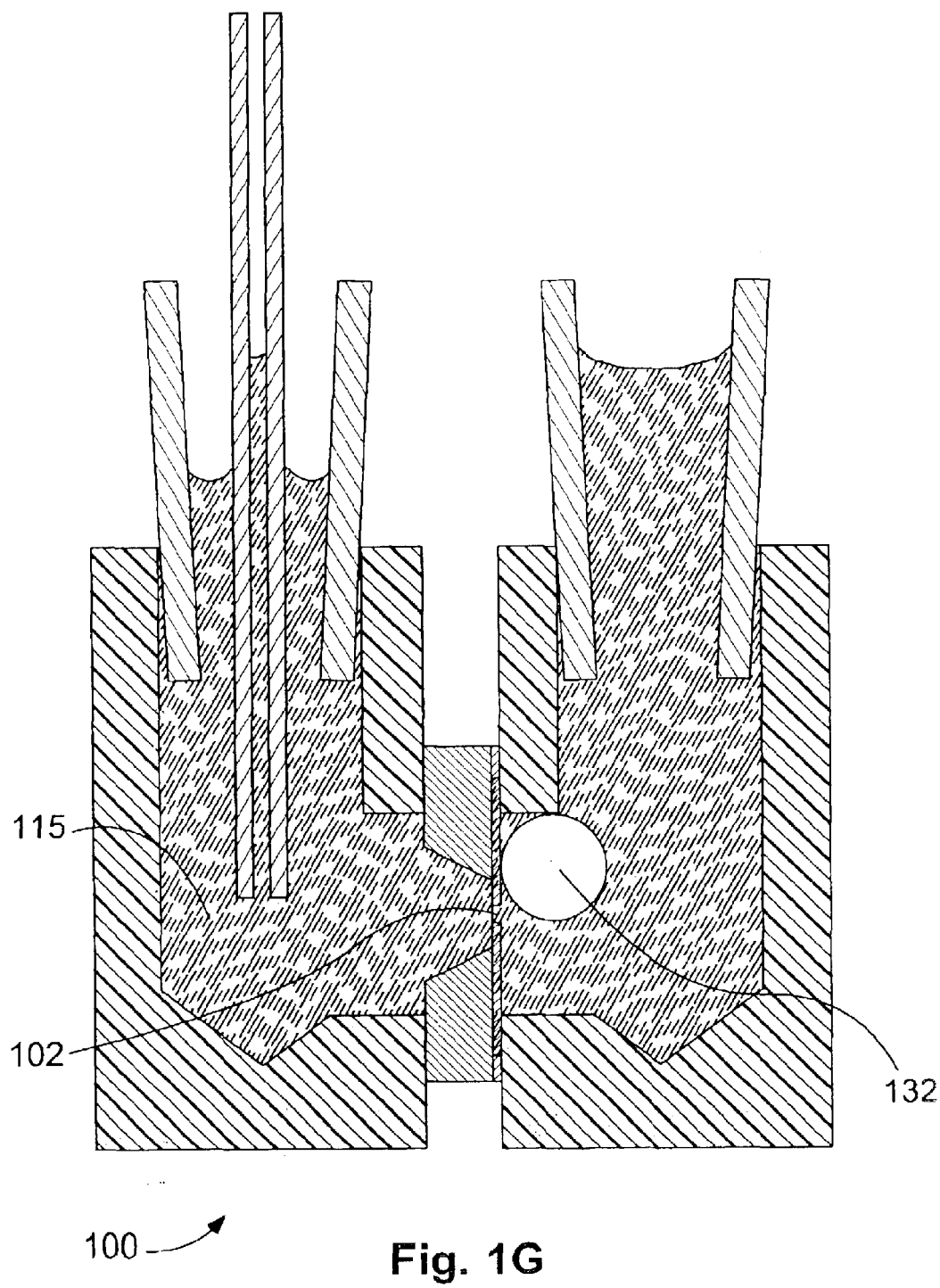
FIG. 1G is a cross-sectional view of the embodiment of FIG. 1A taken along section line 101 at another point in time.

FIG. 1G shows embodiment 100 at a time subsequent to the time of FIG. 1F. Ambient atmosphere 133 has been increased to the original atmospheric pressure. Bubble 130 has completely exited embodiment 100, chamber 115 has filled with liquid, and bubble 132 has shrunk to its original size and returned to a position near its original position. Because bubble 130 has been removed, nanopore 102 is no longer blocked.

Figure 1H:
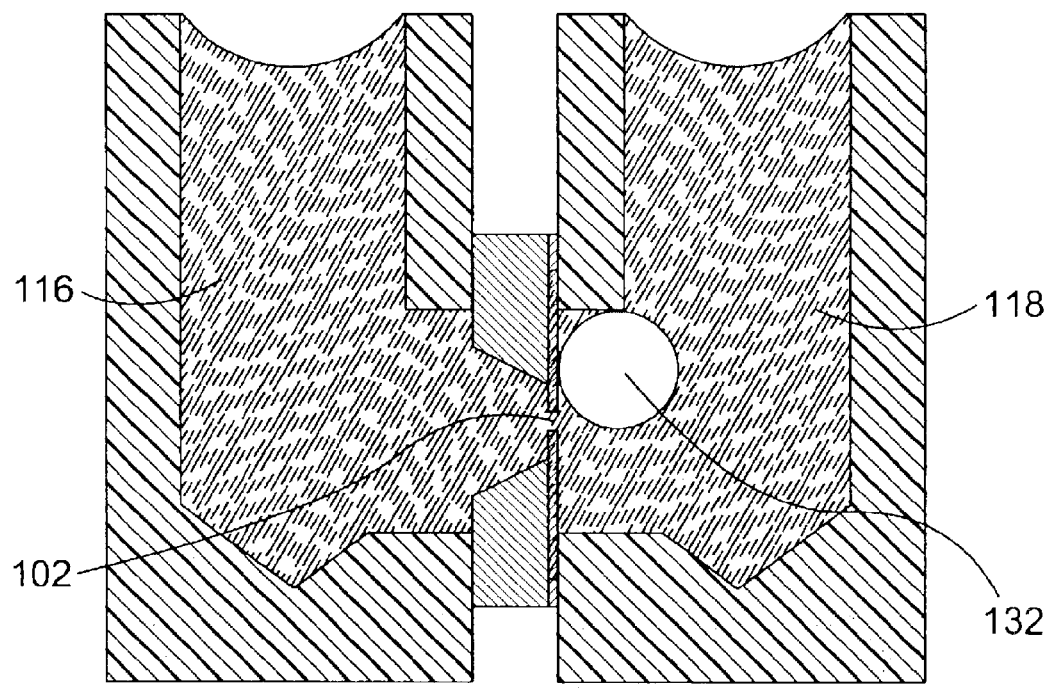
FIG. 1H is a cross-sectional view of the embodiment of FIG. 1A taken along section line 101 at another point in time.

FIG. 1H shows embodiment 100 at a time subsequent to the time of FIG. 1G. Embodiment 100 has been removed from the vacuum chamber, and tubes 120, 122, and 124 have been removed. Bubble 132 does not block nanopore 102, and access to the nanopore is obtainable through channels 116 and 118.

Figure 2A:
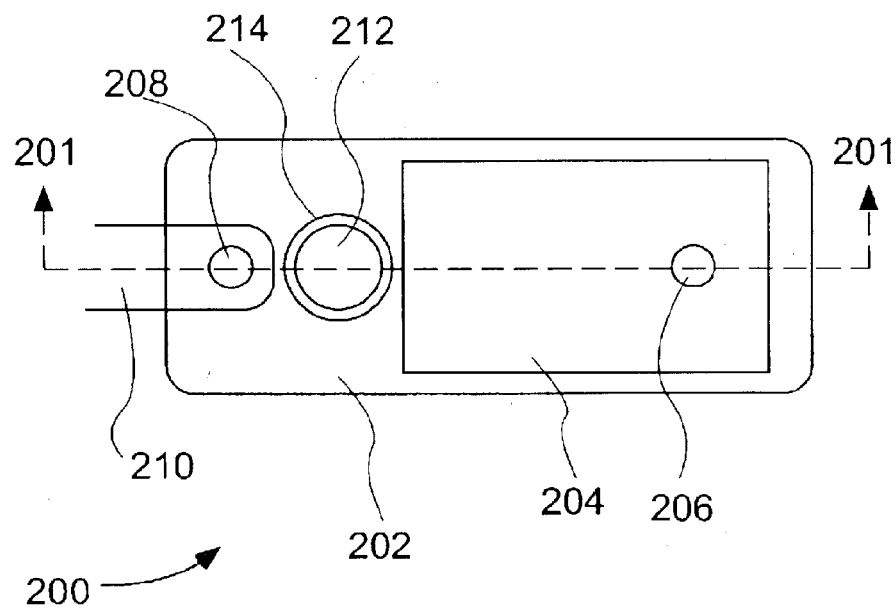
FIG. 2A is a wireframe view of one embodiment of the present invention.
Figure 2B:
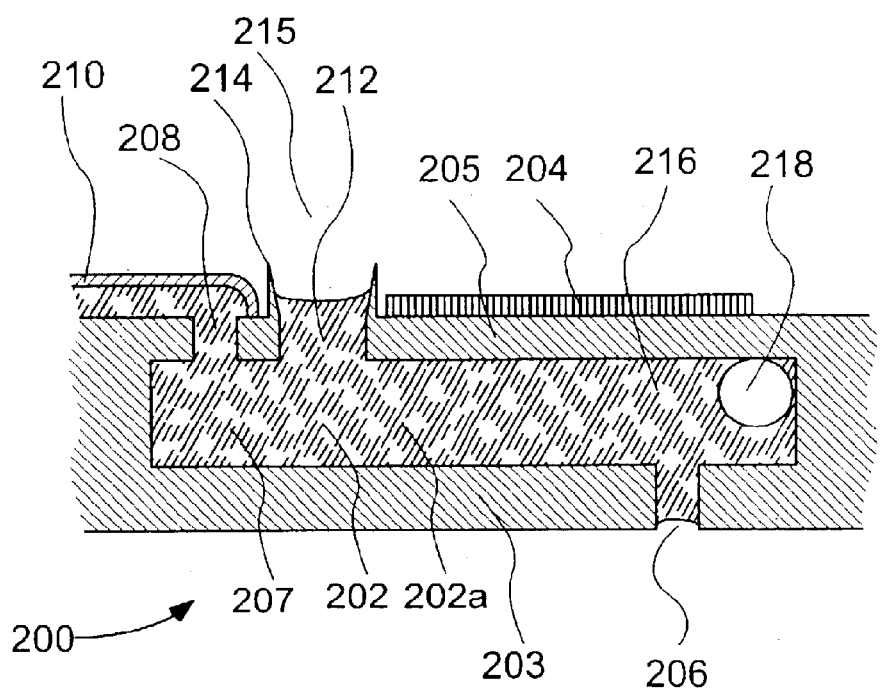
FIG. 2B is a cross-sectional view of the embodiment of FIG. 2A taken along section line 201 at one point in time.

FIGS. 2A–2G illustrate, by way of example and not limitation, an embodiment 200 of the invention as it applies to priming a piezoelectric inkjet firing chamber. As mentioned above, FIG. 2A is a wireframe view of embodiment 200, and section line 201 denotes the cross section of embodiment 200 shown at sequential time steps in FIGS. 2B–2G. FIG. 2B corresponds in time to FIG. 2A, while FIGS. 2C–2G correspond to subsequent times.

In embodiment 200 as illustrated in FIGS. 2A and 2B, firing chamber 202 comprises firing chamber volume 202$a$, which is surrounded by firing chamber walls 203. Piezoelectric actuator 204 is adjacent to wall area 205 and, during normal operation of the inkjet, causes ink to be ejected from firing orifice 206 to a substrate, not shown, such as paper or glass. Liquid 207, for example, ink, is supplied to firing chamber 202 through orifice 208 from source channel 210. For purposes of the present invention, barrier orifice 212 and an exit region comprising aperture 214 and ambient volume 215 are included with the inkjet firing chamber. Region 216 may be occupied in part by gaseous bubble 218, which is present in spite of careful filling procedures, or which originates within the liquid 207 because of outgassing of dissolved gas. Gaseous bubble 218 can prevent the inkjet from firing because it introduces a gas elasticity to the system; the situation is similar to the problem of air in a brake line of an automobile which can cause the brakes to work poorly.

In conventional inkjet structures, which do not have features 212, 214, and 215, removal of such a bubble is problematic and would be attempted by flushing large quantities of ink from source channel 210, through the firing chamber volume 202$a$, and out the firing orifice 206, in the hope of carrying bubble 218 out of the firing chamber volume 202$a$ through the firing orifice 206. The present invention avoids wasting ink and removes the bubble 218 through barrier region 212 and to the exit region comprising aperture 214 and ambient volume 215. Firing orifice 206 corresponds to an aperture for dispensing droplets of liquid from chamber 202. It should be understood that the energy potential of such aperture is higher than that of the barrier region and exit region so that liquid does not exit the aperture during the bubble removal process.

Figure 2C:
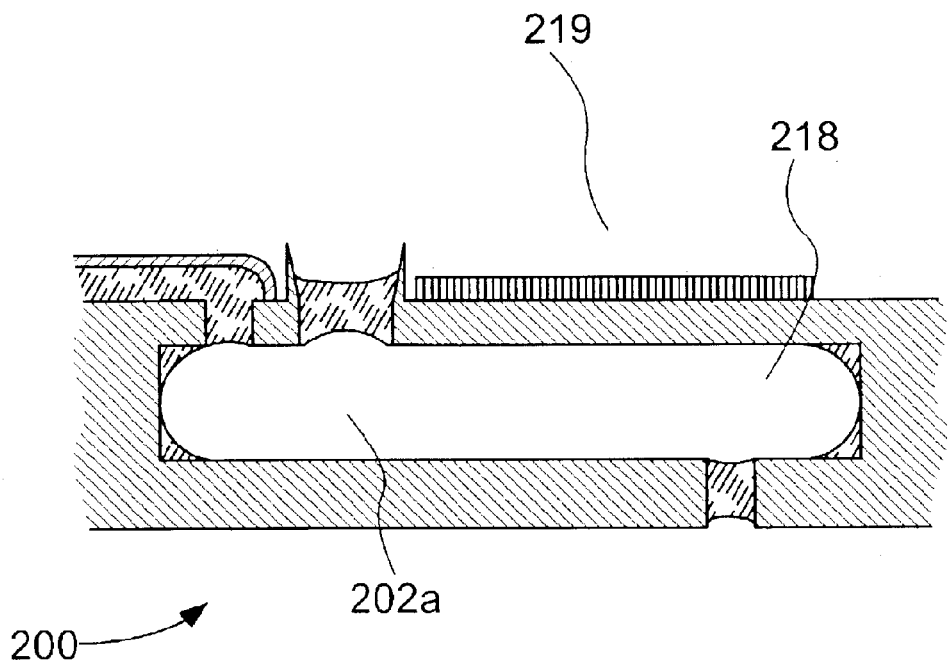
FIG. 2C is a cross-sectional view of the embodiment of FIG. 2A taken along section line 201 at another point in time.

FIG. 2C illustrates embodiment 200 at a time subsequent to the time of FIG. 2B. Embodiment 200 has been placed in a vacuum chamber, not shown, and ambient pressure 219 has been reduced in pressure to a value below atmospheric pressure by pumping on the vacuum chamber using a vacuum pump, not shown. As ambient pressure 219 is reduced, bubble 218 expands in volume to fill the firing chamber volume 202$a$.

Figure 2D:
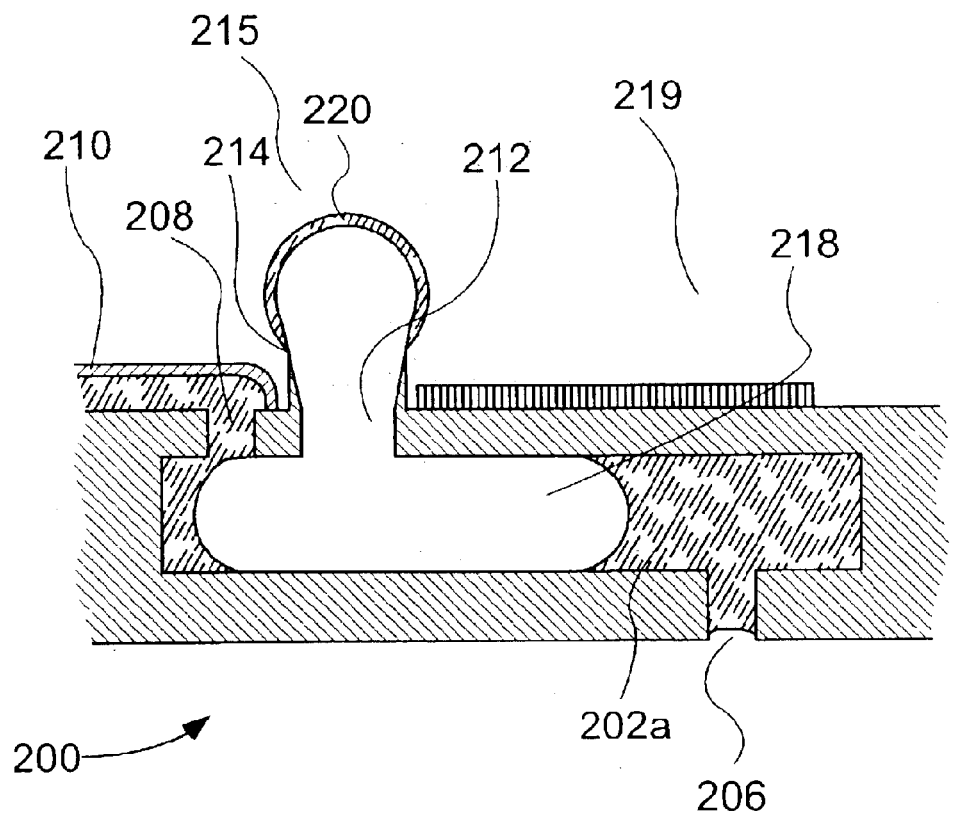
FIG. 2D is a cross-sectional view of the embodiment of FIG. 2A taken along section line 201 at another point in time.

FIG. 2D illustrates embodiment 200 at a time subsequent to the time of FIG. 2C. Pressure 219 has been further reduced, and bubble 218 has extruded through barrier orifice 212. Bubble boundary 220 is attached at aperture 214, and extends outward into ambient volume 215. As explained above, bubble 218 has not extruded through orifice 206 or orifice 208 because those two orifices present higher energy potential barriers to bubble extrusion than does barrier orifice 212. Additional liquid has entered firing chamber volume 202$a$ through orifice 208 from source channel 210, has crept past the edges of the bubble 218 where the bubble 218 fails to completely occupy the corners of the firing chamber volume 202$a$ and has filled in the volume firing chamber volume 202$a$ near firing orifice 206 as the bubble moves from right to left to the exit region comprising aperture 214 and ambient volume 215.

Figure 2E:
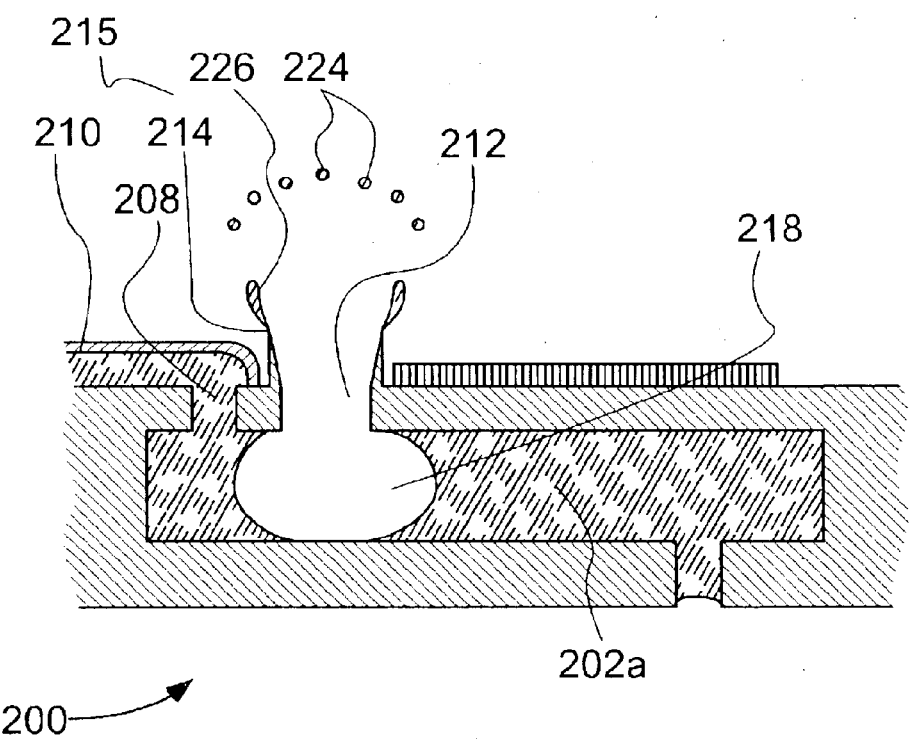
FIG. 2E is a cross-sectional view of the embodiment of FIG. 2A taken along section line 201 at another point in time.

FIG. 2E illustrates embodiment 200 at a time subsequent to the time of FIG. 2D. Pressure 219 has been further reduced, and bubble 218 has burst. The remains of bubble boundary 220 are drawn as free droplets 224 and fringe 226 located adjacent to aperture is 214, but no attempt has been made to accurately portray the bursting process. Bubble 218 is still in the process of exiting from firing chamber 202 to ambient volume 215.

Figure 2F:
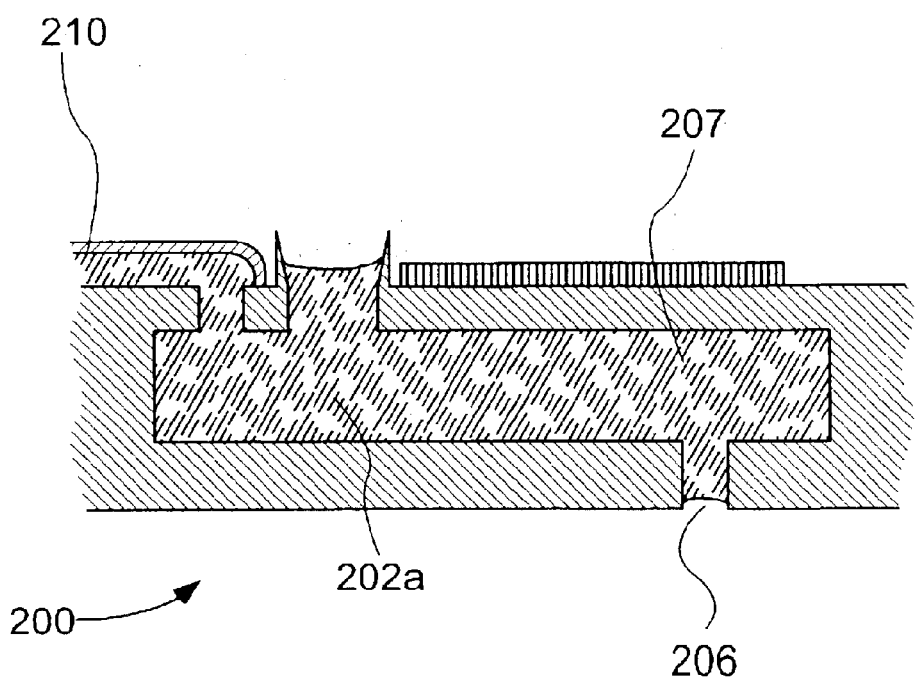
FIG. 2F is a cross-sectional view of the embodiment of FIG. 2A taken along section line 201 at another point in time.

FIG. 2F illustrates embodiment 200 after the bubble has exited firing chamber volume 202. The firing chamber volume 202$a$ is completely refilled with liquid 207 from source channel 210, and no bubbles are present.

Figure 2G:
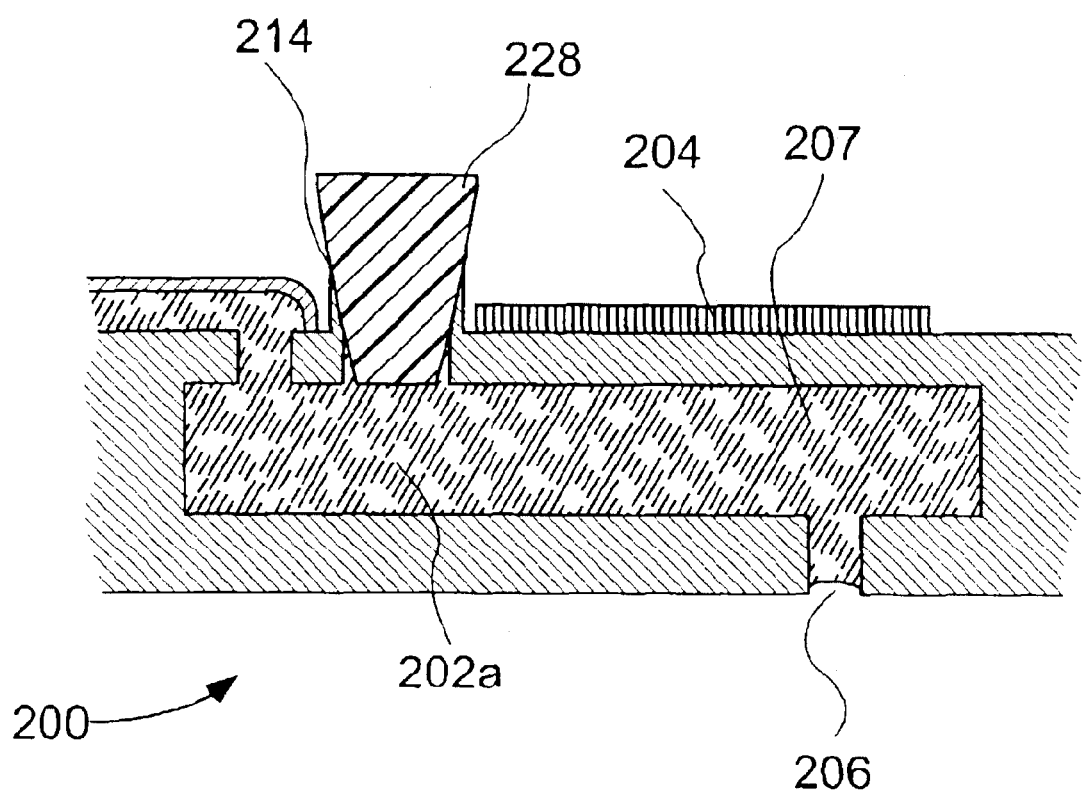
FIG. 2G is a cross-sectional view of the embodiment of FIG. 2A taken along section line 201 at another point in time.

FIG. 2G illustrates embodiment 200 after a plug 228 has been secured in aperture 214. The plug supplies sufficient rigidity to the firing chamber so that mechanical pulses originating at piezoelectric driver 204 can expel droplet of liquid 207 from firing orifice 206.

Another embodiment of the present invention is an apparatus comprising a chamber, a source of liquid in fluid communication with the chamber, a barrier region in fluid communication with the chamber, an exit region in fluid communication with the chamber, and an aperture. The aperture may be selected from the group consisting of micropores and nanopores. The chamber may be part of a microfluidic system, which may be selected from the group consisting of droplet dispensing devices and microdevices having artificial nanopores. The apparatus may further include a plug for sealing the exit region after removal of a bubble. The plug may be attached by friction fitting, screw fitting, luer-lock fitting, glue, solder, brazing, welding, compression fitting, clamp fitting, and the like. The plug may be constructed any of a wide variety of rigid or flexible materials including rubbers, elastomers, metals, polymers, ceramics, glasses, and the like.

All publications and patent applications cited in this specification are herein incorporated by reference as if each individual publication or patent application were specifically and individually indicated to be incorporated by reference, except insofar as they may conflict with those of the present application (in which case the present application prevails). Methods recited herein may be carried out in any order of the recited events, which is logically possible, as well as the recited order of events.

The aforementioned description includes theories and mechanisms by which the invention is thought to work. It should be noted, however, that such proposed theories and mechanisms are not required and the scope of the present invention should not be limited by any particular theory and/or mechanism.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims. Furthermore, the foregoing description, for purposes of explanation, used specific nomenclature to provide a thorough understanding of the invention. However, it will be apparent to one skilled in the art that the specific details are not required in order to practice the invention. Thus, the foregoing descriptions of specific embodiments of the present invention are presented for purposes of illustration and description; they are not intended to be exhaustive or to limit the invention to the precise forms disclosed. Many modifications and variations are possible in view of the above teachings. The embodiments were chosen and described in order to explain the principles of the invention and its practical applications and to thereby enable others skilled in the art to utilize the invention.

What is claimed is:

1. A method for removing a gaseous bubble confined in a microvolume of liquid in a chamber, said method comprising:
    (a) providing in fluid communication with said chamber a source of said liquid and a barrier region and an exit region wherein said source of said liquid has an energy potential as regards movement of said gaseous bubble that is higher than the energy potential of said barrier region, said barrier region has a higher energy potential than said chamber, and said chamber has a higher energy potential than said exit region, and
    (b) reducing the energy potential within said chamber, said source, said barrier region, and said exit region by an amount such that the energy within said gaseous bubble is sufficient to displace said gaseous bubble from said chamber through said barrier region and out said exit region and to fill said chamber with said liquid from said source.

2. A method according to claim 1 wherein said energy potential is reduced by reducing ambient pressure surrounding said chamber.

3. A method according to claim 1 wherein said chamber comprises an aperture having an energy potential greater than the energy potential of said barrier region and said exit region.

4. A method according to claim 1 wherein said aperture is selected from the group consisting of micropores and nanopores.

5. A method according to claim 3 wherein said chamber is part of a microfluidic system.

6. A method according to claim 5 wherein said microfluidic system is selected from the group consisting of droplet dispensing devices and microdevices having artificial nanopores.

7. A method according to claim 3 wherein said exit region is sealed subsequent to filling of said chamber with said liquid.

8. A method of introducing a liquid into a chamber and avoiding formation of or removing a gaseous bubble therein, said method comprising:
    (a) introducing said liquid into said chamber from a source of said liquid wherein said source, a barrier region and an exit region are in fluid communication with said chamber and wherein said source of said liquid has an energy potential as regards movement of said gaseous bubble that is higher than the energy potential of said barrier region, said barrier region has a higher energy potential than said chamber, and said chamber has a higher energy potential than said exit region, and
    (b) reducing the energy potential within said chamber, said source, said barrier region, and said exit region by an amount sufficient that the energy within said gaseous bubble is sufficient to displace said gaseous bubble from said chamber through said barrier region and out said exit region and to fill said chamber with said liquid from said source.

9. A method according to claim 8 wherein said energy potential is reduced by reducing ambient pressure surrounding said chamber.

10. A method according to claim 8 wherein said chamber comprises an aperture having an energy potential greater than the energy potential of said barrier region and said exit region.

11. A method according to claim 8 wherein said aperture is selected from the group consisting of micropores and nanopores.

12. A method according to claim 10 wherein said chamber is part of a microfluidic system.

13. A method according to claim 12 wherein said microfluidic system is selected from the group consisting of droplet dispensing devices and microdevices having artificial nanopores.

14. A method according to claim 10 wherein said exit region is sealed subsequent to filling of said chamber with said liquid.

* * * * *